United States Patent
Lui et al.

(10) Patent No.: US 7,977,494 B2
(45) Date of Patent: Jul. 12, 2011

(54) METHOD FOR PRODUCING SUBSTITUTED PYRAZOLECARBOXYLIC ACID CHLORIDES

(75) Inventors: Norbert Lui, Odenthal (DE); Jens-Dietmar Heinrich, Burscheid (DE); Alexander Straub, Wuppertal (DE); Thomas Wollner, Cologne (DE); James Mark Ford, Schmitten (DE)

(73) Assignee: Bayer Cropscience AG, Monheim (DE)

( * ) Notice: Subject to any disclaimer, the term of this patent is extended or adjusted under 35 U.S.C. 154(b) by 223 days.

(21) Appl. No.: 12/523,335

(22) PCT Filed: Jan. 9, 2008

(86) PCT No.: PCT/EP2008/000091
§ 371 (c)(1),
(2), (4) Date: Jul. 16, 2009

(87) PCT Pub. No.: WO2008/086962
PCT Pub. Date: Jul. 24, 2008

(65) Prior Publication Data
US 2010/0041899 A1    Feb. 18, 2010

(30) Foreign Application Priority Data

Jan. 18, 2007  (DE) .................. 10 2007 002 674

(51) Int. Cl.
*C07D 231/14* (2006.01)
(52) U.S. Cl. .................................................. 548/374.1
(58) Field of Classification Search ................ None
See application file for complete search history.

(56) References Cited

U.S. PATENT DOCUMENTS 5,675,016 A    10/1997    Gallenkamp et al.

FOREIGN PATENT DOCUMENTS

| JP | 02085257 | 3/1990 |
| JP | 07010845 | 1/1995 |
| JP | 7070076 | 3/1995 |
| WO | 93/11117 | 6/1993 |

OTHER PUBLICATIONS

International Search Report from PCT/EP2008/000091; dated Apr. 2, 2009; (5 pages).
Huppatz "Systemic Fungicides. The synthesis of Certain Pyrazole Analogues of Caboxin," in Aust. J. Chem., 1983, 36, 135-47.

*Primary Examiner* — Kamal Saeed
(74) *Attorney, Agent, or Firm* — Baker Donelson Bearman, Caldwell & Berkowitz, PC

(57) ABSTRACT

The present invention relates to a process for preparing substituted pyrazolyl chlorides by chlorinating aldehydes of the formula (II) under free-radical conditions.

16 Claims, No Drawings

METHOD FOR PRODUCING SUBSTITUTED PYRAZOLECARBOXYLIC ACID CHLORIDES

CROSS REFERENCE TO RELATED APPLICATIONS

This application is a §371 National Stage Application of PCT/EP2008/000091 filed Jan. 9, 2008 which claims priority from German Application 10 2007 002 674.0 filed Jan. 18, 2007.

BACKGROUND OF THE INVENTION

1. Field of the Invention

The present invention relates to a process for preparing substituted pyrazolyl chlorides by chlorinating aldehydes of the formula (II) under free-radical conditions.

2. Description of Related Art

Pyrazolyl chlorides are important units for preparing active crop protection ingredients.

Pyrazolyl chlorides are typically prepared by reacting carboxylic acids with a chlorinating agent. One advantage of this process is based on the fact that the corresponding carboxylic acids are easy to obtain and hence available on the industrial scale. This prerequisite is not satisfied in the preparation of the substituted pyrazolyl chlorides, since the corresponding carboxylic acids are not readily available.

For instance, the pyrazole-4-carboxylic acids are prepared from pyrazole-4-carboxaldehydes (J. L. Huppatz: Aust. J. Chem. 36, 135-147 (1983)) with potassium permanganate according to scheme I. One problem in the industrial implementation of this oxidation is the formation of large amounts of manganese dioxide.

Scheme I

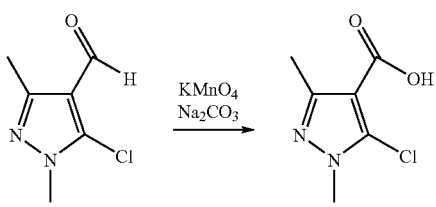

JP 7070076 describes the preparation of pyrazole-4-carboxylic acid by reaction of pyrazole-4-carbaldehyde with hydrogen peroxide and sodium chloride in an aqueous system under acidic conditions and in the presence or absence of a phase transfer catalyst. The space-time yields are low and the process is difficult from a safety technology point of view owing to hydrogen peroxide.

The pyrazolecarbonyl chloride then has to be prepared from the pyrazole-4-carboxylic acid in a second step with the aid of a chlorinating agent, for example thionyl chloride.

With regard to the disadvantages and problems outlined above, there is the need to provide a process which, in one step proceeding from substituted pyrazolecarboxaldehydes, makes the corresponding substituted carbonyl chlorides available with high yields and high selectivity.

SUMMARY OF THE INVENTION

The present invention therefore provides a process for preparing substituted pyrazolecarbonyl chlorides of the general formula (I)

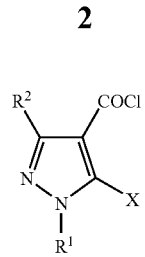

in which

R$^1$ is hydrogen, alkyl, alkoxyalkyl, unsubstituted or substituted aryl, unsubstituted or substituted aralkyl, alkoxyalkyl, unsubstituted or substituted aryl, unsubstituted or substituted alkaryl, unsubstituted or substituted heteroaryl and haloalkyl, R$^2$ is hydrogen, halogen, alkyl, alkoxyalkyl, unsubstituted or substituted aryl, unsubstituted or substituted aralkyl, unsubstituted or substituted heteroaryl and haloalkyl, X is fluorine, chlorine or bromine, characterized in that aldehydes of the formula (II)

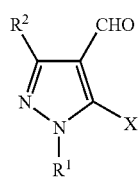

in which R$^1$, R$^2$ and X are each as defined above are reacted with a chlorinating agent under free-radical conditions.

DETAILED DESCRIPTION OF A PREFERRED EMBODIMENT

General Definitions

In connection with the present invention, the term "halogen" (X), unless defined otherwise, includes those elements which are selected from the group consisting of fluorine, chlorine, bromine and iodine, preference being given to using fluorine, chlorine and bromine, and particular preference to using fluorine and chlorine.

Optionally substituted radicals may be mono- or polysubstituted, and the substituents may be the same or different in the case of polysubstitutions.

Alkyl groups substituted by one or more halogen atoms are, for example, selected from trifluoromethyl (CF$_3$), difluoromethyl (CHF$_2$), CF$_3$CH$_2$, ClCH$_2$, CF$_3$CCl$_2$.

In connection with the present invention, unless defined differently, alkyl groups are linear, branched or cyclic hydrocarbon groups which may optionally have one, two or more single or double unsaturations, or one, two or more heteroatoms which are selected from O, N, P and S. In addition, the inventive alkyl radicals may optionally be substituted by further groups which are selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), where R' may be hydrogen or a C$_{1-12}$-alkyl group, preferably C$_{2-10}$-alkyl group, more preferably C$_{3-8}$-alkyl group.

The definition "C$_{1-12}$-alkyl" encompasses the widest range defined herein for an alkyl radical. Specifically, this definition includes, for example, the meanings of methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

In connection with the present invention, unless defined differently, aryl radicals are aromatic hydrocarbon radicals which may have one, two or more heteroatoms which are selected from O, N, P and S, and may optionally be substituted by further groups which are selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), where R' may be hydrogen or a $C_{1-12}$-alkyl group, preferably $C_{2-10}$-alkyl group, more preferably $C_{3-8}$-alkyl group.

The definition "$C_{5-18}$-aryl" encompasses the widest range defined herein for an aryl radical having from 5 to 18 skeleton carbon atoms. Specifically, this definition includes, for example, the meanings of cyclopentadienyl, phenyl, cycloheptatrienyl, cyclooctatetraenyl, naphthyl and anthracenyl.

In connection with the present invention, unless defined differently, heteroaryl radicals are aromatic hydrocarbon radicals which have one, two, three or more heteroatoms which are selected from O, N, P and S and may optionally be substituted by further groups which are selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), where R' may be hydrogen or a $C_{1-12}$-alkyl group, preferably $C_{2-10}$-alkyl group, more preferably $C_{3-8}$-alkyl group.

The definition "$C_{5-18}$-heteroaryl" encompasses the widest range defined herein for an aryl radical having 5 to 18 skeleton carbon atoms, where the skeleton carbon atoms may be replaced by the heteroatoms mentioned above. Specifically, this definition encompasses, for example, the meanings of 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl und 1,3,4-triazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

In connection with the present invention, unless defined differently, arylalkyl radicals (aralkyl radicals) are alkyl radicals which are substituted by aryl groups and may have a $C_{1-8}$-alkylene chain and may be substituted in the aryl skeleton or the alkylene chain by one or more heteroatoms which are selected from O, N, P and S, and optionally by further groups which are selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), where R' may be hydrogen or a $C_{1-12}$-alkyl group, preferably $C_{2-10}$-alkyl group, more preferably $C_{3-8}$-alkyl group.

The definition "$C_{7-19}$-aralkyl radical" encompasses the widest range defined herein for an arylalkyl radical having a total of 7 to 19 carbon atoms in the skeleton and alkylene chain. Specifically, this definition comprises, for example, the meanings of benzyl and phenylethyl.

In connection with the present invention, unless defined differently, alkylaryl radicals (alkaryl radicals) are aryl radicals which are substituted by alkyl groups and may have a $C_{1-8}$-alkylene chain and may be substituted in the aryl skeleton or the alkylene chain by one or more heteroatoms which are selected from O, N, P and S, and may optionally be substituted by further groups which are selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), where R' may be hydrogen or a $C_{1-12}$-alkyl group, preferably $C_{2-10}$-alkyl group, more preferably $C_{3-8}$-alkyl group.

The definition "$C_{7-19}$-alkylaryl radical" encompasses the widest range defined herein for an alkylaryl radical having a total of 7 to 19 carbon atoms in the skeleton and alkylene chain. Specifically, this definition includes, for example, the meanings of tolyl, 2,3-, 2,4-, 2,5-, 2,6-, 3,4- or 3,5-dimethylphenyl.

It is possible by the process according to the invention to prepare acid chlorides of the formula (I) in good yields in one stage from the corresponding aldehydes of the formula (II). This is surprising since the chlorination of compounds of the formula (II) with chlorinating agents in the absence of a free-radical initiator proceeds by a completely different reaction route, which is shown in scheme II.

Scheme II

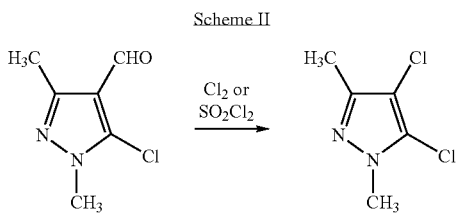

Preference is given to performing the process according to the invention using the aldehyde of the formula (II) in which the radicals specified are each defined as follows. The preferred, particularly preferred and very particularly preferred definitions apply to all compounds in which the particular radicals occur.

In formula (I) and (II), $R^1$ is hydrogen, $C_{1-12}$-alkyl, $C_{1-4}$-alkoxy-$C_{1-12}$-alkyl, unsubstituted or substituted $C_{5-18}$-aryl, unsubstituted or substituted $C_{5-19}$-aralkyl, unsubstituted or substituted $C_{5-19}$-alkaryl, unsubstituted or substituted $C_{5-18}$-heteroaryl and $C_{1-12}$-haloalkyl having 1 to 5 halogen atoms; preferably $C_1$- to $C_3$-alkyl, more preferably methyl;

$R^2$ is hydrogen, halogen, $C_{1-12}$-alkyl, $C_{1-4}$-alkoxy-$C_{1-12}$-alkyl, unsubstituted or substituted aryl, unsubstituted or substituted $C_{5-19}$-aralkyl, unsubstituted or substituted $C_{5-19}$-alkaryl, unsubstituted or substituted $C_{5-18}$-heteroaryl and $C_{1-12}$-haloalkyl having 1 to 5 halogen atoms; preferably hydrogen, halogen, $C_{1-5}$-alkyl and $C_{1-5}$-haloalkyl, more preferably methyl;

X is fluorine, chlorine or bromine, preferably fluorine and chlorine, more preferably chlorine.

The aldehydes of the formula (II) to be used as starting materials in the performance of the process according to the invention have been described before in the prior art or can be obtained by known processes, for example by Vilsmeier-Haack reaction with DMF and POCl$_3$.

The substituted aldehyde of the formula (II) and the chlorinating agent are typically used in a molar ratio of from 1:3 to 3:1, preferably 1:1.4 to 1:1.

The chlorinating agent used may be chlorine or a chlorine-releasing agent. The reaction can optionally be performed in the presence of an inert diluent gas, for example nitrogen, carbon dioxide or noble gases. Suitable chlorinating agents, without making any claim to completeness, are, for example, $Cl_2$, $SO_2Cl_2$, $SOCl_2$, N-chlorosuccinimide or a mixture thereof. Preference is given to using $Cl_2$, $SO_2Cl_2$ or a mixture thereof as the chlorinating agent. Particular preference is given to $Cl_2$ as the chlorinating agent.

According to the present invention, the chlorination is effected under free-radical conditions. The prequisite for this is the formation of chlorine radicals.

Free radicals can be formed by different methods which have been described before in the prior art and are familiar to the person skilled in the art.

Free radicals can in principle be obtained in three ways: (a) by homolytic bond breakage, (b) by reaction with other free radicals and (c) by single electron transfer. In the case of generation of free radicals by homolysis, labile bonds are split thermally, photochemically or radiolytically.

In connection with the present invention, the free-radical conditions are preferably created by the reaction of the substituted aldehydes with the chlorinating agent in the presence of a free-radical initiator or by irradiation.

It is known that organic peroxides or azo compounds, under the action of heat and/or light, decompose to free radicals which initiate the free-radical chlorination.

Examples, without any claim to completeness, of suitable peroxides and azo compounds are tert-butyl hydroperoxide, dibenzoyl peroxide, di(4-tert-butylcyclohexyl) peroxydicarbonate, 2,2'-azobis(isobutyronitrile), dimethyl 2,2'-azobis (isobutyrate), 2,2'-azobis(2,4-dimethylvaleronitrile), di(2-ethylhexyl) peroxydicarbonate, tert-butyl peroxypivalate, tert-amyl peroxy-2-ethylhexanoate, tert-butyl peroxy-2-ethylhexanoate.

Preference is given to using the following free-radical initiators: 2,2'-azobis(isobutyronitrile), 2,2'-azobis(2,4-dimethylvaleronitrile), di(2-ethylhexyl) peroxydicarbonate, tert-amyl peroxy-2-ethylhexanoate, tert-butyl peroxy-2-ethylhexanoate. The free-radical initiator is used typically in an amount of 0.01 to 1 mol %, preferably 0.1 to 0.5 mol %, based on the aldehyde of the formula (II).

In an alternative embodiment of the invention, the free radicals can also be generated by irradiation with electromagnetic radiation, preferably with light or X-radiation. For this purpose, it is possible to use, for example, mercury lamps.

The substituted aldehydes (II) are reacted with the chlorinating agents typically in the presence of a diluent which behaves inertly under the prevailing reaction conditions. The diluents used may, for example, be mono- or polychlorinated aliphatic or aromatic hydrocarbons or mixtures thereof. Examples of suitable diluents are chlorobenzene, dichlorobenzenes, trichlorobenzenes, chlorotoluenes, chlorobenzotrifluorides, methylene chloride, dichloroethane, chloroform, carbon tetrachloride. Preferred diluents are chlorobenzene, 1,2-dichlorobenzene, 1,3-dichlorobenzene, 1,4-dichlorobenzene, 1,2,3-trichlorobenzene, 1,2,4-trichlorobenzene, 4-chlorotrifluoromethylbenzene, 1,3,5-trichlorobenzene, 2-chlorotoluene, 3-chlorotoluene, 4-chlorotoluene or a mixture thereof. Particular preference is given to using chlorobenzene.

The diluent is used typically in a ratio of 20:1 to 1:20, preferably 10:1 to 1:10, based on the substituted aldehyde (II).

The reaction of the substituted aldehyde (II) with the chlorinating agent can be performed, for example, at −10 to 130° C.; preference is given to temperatures of 0-90° C.

An acid scavenger can optionally be added to the reaction mixture. The acid scavengers used may, for example, be potassium carbonate, sodium carbonate, calcium carbonate, potassium hydrogencarbonate, sodium hydrogencarbonate, sodium hydroxide, potassium hydroxide. These acid scavengers may also be used as an aqueous solution.

The substituted pyrazolyl chlorides (I) can be isolated by customary workup methods. In this context, the melting and boiling points of the products are crucial and determine whether the product is distilled or isolated by filtration. Distillative workup is preferred.

The process according to the invention can be performed batchwise or continuously. The process can be performed under standard pressure, reduced pressure or elevated pressure.

The process according to the invention for preparing substituted pyrazolyl chlorides is described in the examples which follow, which further illustrate the above description. However, the examples should not be interpreted in a restrictive manner.

PREPARATION EXAMPLES

Comparative Example

Chlorination without Free Radicals

To 300 g of a 22.7% solution of 5-chloro-1,3-dimethyl-1H-pyrazole-4-carbaldehyde in 1,2-dichlorobenzene are added dropwise at 80° C. 58 g of sulphuryl chloride within 120 minutes. After the metered addition has ended, the reaction solution is stirred for a further 3 hours. The reaction solution is cooled to 20° C. and the solution is analyzed by GC. 4,5-Dichloro-1,3-dimethyl-1H-pyrazole has formed quantitatively.

Example 1

To a solution of 48.5 g of 5-chloro-1,3-dimethyl-1H-pyrazole-4-carbaldehyde in 230 ml of chlorobenzene are added 36 g of sodium carbonate. Subsequently, 3.9 g of 2,2-azoisobutyronitrile (AIBN) are added at 60° C., and, within 4 hours, 24 g of chlorine gas are introduced and a further 6 g of AIBN are added. After the gas introduction has ended, the reaction solution is stirred for a further 30 minutes. The solid is filtered off and washed with a little chlorobenzene. After the solvent has been removed, 5-chloro-1,3-dimethyl-1H-pyrazole-4-carbonyl chloride is obtained in a yield of 74%.

Example 2

To a solution of 48 g of 5-chloro-1,3-dimethyl-1H-pyrazole-4-carbaldehyde in 230 ml of chlorobenzene are added 36.5 g of sodium carbonate. Subsequently, 1.2 g of bis(tert-butylcyclohexyl) peroxycarbonate are added at 20° C. and the mixture is heated to 40° C. Within 4 hours, 24 g of chlorine gas are introduced. After the gas introduction has ended, the reaction solution is stirred at 40° C. for a further 30 minutes. The solid is filtered off and washed with a little chlorobenzene. After removal of the solvent, 5-chloro-1,3-dimethyl-1H-pyrazole-4-carbonyl chloride is obtained in a yield of 68%.

Example 3

To a solution of 48 g of 5-chloro-1,3-dimethyl-1H-pyrazole-4-carbaldehyde in 230 ml of chlorobenzene under protective gas are added 51.8 g of potassium carbonate. Subsequently, while illuminating with a mercury lamp, 24 g of chlorine gas are introduced at 20° C. within 4 hours. After the gas introduction has ended, the reaction solution is stirred with illumination at 20° C. for a further 20 minutes. The solid is filtered off and washed with a little chlorobenzene. After the solvent has been removed, 5-chloro-1,3-dimethyl-1H-pyrazole-4-carbonyl chloride is obtained in a yield of 95%.

Example 4

To a solution of 48 g of 5-chloro-1,3-dimethyl-1H-pyrazole-4-carbaldehyde in 195 ml of dichlorobenzene under protective gas are added 39.8 g of sodium carbonate. Subsequently, while illuminating with a mercury lamp, 24 g of chlorine gas are introduced at 20° C. within 3.5 hours. After the gas introduction has ended, the reaction solution is stirred with illumination at 20° C. for a further 20 minutes. The solid is filtered off and washed with a little dichlorobenzene. After the solvent has been removed, 5-chloro-1,3-dimethyl-1H-pyrazole-4-carbonyl chloride is obtained in a yield of 87%.

Example 5

To a solution of 48 g of 5-chloro-1,3-dimethyl-1H-pyrazole-4-carbaldehyde in 230 ml of chlorobenzene under protective gas, 19.2 g of chlorine gas are introduced while illuminating with a mercury lamp at 30° C. within 4 hours. After the gas introduction has ended, the reaction solution is stirred with illumination at 30° C. for a further 20 minutes. The reaction solution is cooled to 5° C. and the solid is filtered off and washed with a little chlorobenzene. After the solvent has been removed, 5-chloro-1,3-dimethyl-1H-pyrazole-4-carbonyl chloride is obtained in a yield of 87%.

Example 6

Simultaneously, 68 g of sulphuryl chloride and 70.5 g of a 2.5% solution of 2,2-azoisobutyronitrile (AIBN) are added dropwise at 80° C. to 300 g of a 22.7% solution of 5-chloro-1,3-dimethyl-1H-pyrazole-4-carbaldehyde in 1,2-dichlorobenzene within 4 hours. After the metered addition has ended, the reaction solution is stirred for a further 2 hours. After removal of the solvent, 5-chloro-1,3-dimethyl-1H-pyrazole-4-carbonyl chloride is obtained in a yield of 72%.

Example 7

Initial charging of 11 g of a 10% solution of 5-chloro-1,3-dimethyl-1H-pyrazole-4-carbaldehyde in 1,2-dichlorobenzene at 10° C., is followed by addition of a 4.6 g of potassium carbonate in 20 ml of water. At 10° C., while illuminating with a mercury lamp, 8 g of chlorine gas are introduced within 1 hour. After the gas introduction has ended, the reaction solution is admixed with water, and the organic phase is removed and washed with water. After removal of the solvent, 5-chloro-1,3-dimethyl-1H-pyrazole-4-carbonyl chloride is obtained in a yield of 77%.

The invention claimed is:

1. Process for preparing substituted pyrazolecarbonyl chlorides of formula (I)

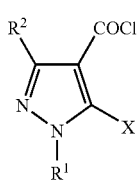

(I)

in which
R$^1$ is hydrogen, alkyl, alkoxyalkyl, unsubstituted or substituted aryl, unsubstituted or substituted aralkyl, unsubstituted or substituted heteroaryl and haloalkyl,
R$^2$ is hydrogen, halogen, alkyl, alkoxyalkyl, unsubstituted or substituted aryl, unsubstituted or substituted aralkyl, unsubstituted or substituted heteroaryl and haloalkyl,
X is fluorine, chlorine or bromine,
comprising reacting in aldehyde of formula (II)

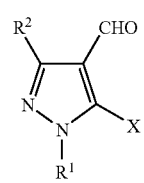

(II)

with a chlorinating agent under free-radical conditions.

2. Process according to claim 1, where
R$^1$ is C$_1$- to C$_3$-alkyl,
R$^2$ is hydrogen, halogen, alkyl and haloalkyl, and
X is chlorine, bromine or fluorine.

3. Process according to claim 1, wherein
R$^1$ is methyl,
R$^2$ is methyl and
X is chlorine or fluorine.

4. Process according to claim 1, wherein the free-radical conditions are generated by the presence of a free-radical initiator or by irradiation.

5. Process according to claim 1, wherein the reaction is performed in the presence of an acid scavenger.

6. Process according to claim 1, wherein the reaction is performed in the presence of an aqueous base.

7. Process according to claim 2, wherein
R$^1$ is methyl,
R$^2$ is methyl and
X is chlorine or fluorine.

8. Process according to claim 2, wherein the free-radical conditions are generated by the presence of a free-radical initiator or by irradiation.

9. Process according to claim 3, wherein the free-radical conditions are generated by the presence of a free-radical initiator or by irradiation.

10. Process according to claim 2, wherein the reaction is performed in the presence of an acid scavenger.

11. Process according to claim 3, wherein the reaction is performed in the presence of an acid scavenger.

12. Process according to claim 4, wherein the reaction is performed in the presence of an acid scavenger.

13. Process according to claim 2, wherein the reaction is performed in the presence of an aqueous base.

14. Process according to claim 3, wherein the reaction is performed in the presence of an aqueous base.

15. Process according to claim 4, wherein the reaction is performed in the presence of an aqueous base.

16. Process according to claim 5, wherein the reaction is performed in the presence of an aqueous base.

* * * * *